United States Patent [19]

Davidson

[11] Patent Number: Plant 6,152

[45] Date of Patent: Apr. 19, 1988

[54] ROSE PLANT NAMED "SMOOTH VELVET"

[75] Inventor: Harvey D. Davidson, Orinda, Calif.

[73] Assignee: Gurney Seed and Nursery Corporation, Yankton, S. Dak.

[21] Appl. No.: 823,586

[22] Filed: Jan. 28, 1986

[51] Int. Cl.[4] ..... A01H 5/00

[52] U.S. Cl. ..... Plt/19

[58] Field of Search ..... Plt./19, 20

*Primary Examiner*—Robert E. Bagwill

*Attorney, Agent, or Firm*—L. S. Van Landingham, Jr.

[57] ABSTRACT

A new rose variety of the hybrid tea class distinctive in its character by being thornless and by having blooms of a dark red color as hereafter shown and described.

1 Drawing Sheet

1

The present invention relates to a new and distinct variety of rose plant of the hybrid tea rose class, which was originated by my crossing "Smooth Lady" as the seed parent with "Red Devil" as pollen parent.

Among the novel characteristics possessed by this new variety which distinguish it from its parents and all other varieties of which I am aware are: (1) Neither thorns nor prickles on the main stems, laterals or leaf stems. (2) A large, well formed dark red flower. (3) A very tall, upright plant habit.

Asexual reproduction of the new rose variety by budding, as performed at McFarland, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g. "53A" is plate "53A" of The Royal Horticultural Society Colour Chart.

American Rose Society Registration commercial appellation: "Smooth Velvet".

Irar and Ciopora appellation: "Hadvelvet".

Parentage: Seedling.

*Seed parent.*—"Smooth Lady".

*Pollen parent.*—"Red Devil".

Class: Hybrid tea.

The following observations are made of specimens grown outdoors in Contra Costa County, Calif., in the month of October.

FLOWER

Blooming habit:

A. Bud:

(1) *Size.*—Medium to large.

(2) *Form.*—Ovoid and pointed.

(3) *Sepals.*—Slender, non-serrated extension ¾ cm beyond bud tip. Color before breaking — 144A; when turned down — 194A.

2

(4) *Peduncle.*—Length — 5 to 6 cm; Surface — smooth, no prickles or hairs; Strength — stiff; Color — 146C flushed 172B.

(5) *Color.*—When sepals first divide — shaded darker than 53A; As petals unfurl — 53A.

B. Bloom:

(1) *Size.*—Average when open — 13 cm.

(2) *Borne.*—Singly, occasionally two to stem.

(3) *Form.*—Tightly cupped, very full, high center remains through maturity, outer petal edges curled.

(4) *Petalage.*—Average number — 38 to 42.

(5) *Color.*—Early open stages — outer side of petals — 53B. inner side — slightly darker than 53A, quite uniform throughout; Aging to 53A.

C. Petals:

(1) *Texture.*—Very thick.

(2) *Appearance.*—Velvety on inside; satiny on outside.

(3) *Form.*—Round and slightly scalloped at center edge.

(4) *Arrangement.*—Regular at all stages.

(5) *Petaloids in center.*—Average 2 to 3.

(6) *Persistance.*—Drop off cleanly.

(7) *Fragrance.*—Light demask.

(8) *Lasting quality.*—Long lasting on bush; good cut flower.

REPRODUCTIVE ORGANS

A. Stamen:

(1) *Arrangement.*—Regularly arranged around styles.

(2) *Number.*—Average 112 to 118.

(3) *Length.*—Average 5 to 7 mm.

(4) *Filaments.*—Color 21C.

(5) *Anthers.*—Color 23B.

(6) *Pollen.*—Color 20B; Viable.

B. Pistil:

(1) *Styles.*—Covered with fine white hairs. Longitudinal striping on each style — color 50B.

(2) *Stigma.*—Color 9D.

(3) *Ovary.*—Not well developed.

C. Hips: Will accept own pollen only, but rarely.

(1) *Shape.*—Globular.

(2) *Color.*—170A when mature.

(3) *Seed.*—Average 4 to 6 per hip; Do not protrude.

PLANT

A. Form: Upright.

B. Growth: Very Vigorous, tall.

*Height.*—2 to 2.5 meters. Considerable spacing between leaves.

C. Foliage: Compound of 3 to 5 leaflets on bloom stem. 5 to 7 leaflets on main canes, very few 7.

(1) *Size.*—Large.

(2) *Quantity.*—Moderate, insufficient obscuring of stems.

(3) *Color.*—New foliage — Upper side 146A with 183B on perimeter of leaf; under side 146B. Old foliage — Upper side 137A; under side 137B.

(4) *Shape.*—Rounded with center pointed.

(5) *Texture.*—Upper side — Leathery and dull. Under side — smooth and dull.

(6) *Edge.*—Uniform, well defined serration.

(7) *Rachis.*—Smooth both upper and lower sides.

(8) *Stipules.*—Medium length with short pointed beard.

D. Wood:

(1) *New wood.*—Color — 173A; Bark — smooth.

(2) *Old wood.*—Color — 146C; Bark — smooth.

E. Thorns: No thorns or prickles on main stems, laterals, rachis or peduncle.

F. Resistance to disease: Mildew and rust — very good. Blackspot — none observed.

G. Winter hardiness: Good.

I claim:

1. A new and distinct variety of rose plant of the hybrid tea class, substantially as shown and described, characterized by its lack of thorns or prickles at any point on the plant which is very tall and upright with dull and disease resistant foliage spaced apart, permitting stem visibility and having dark, full, well formed, velvety red flowers, generally one to a stem, which repeat moderately.

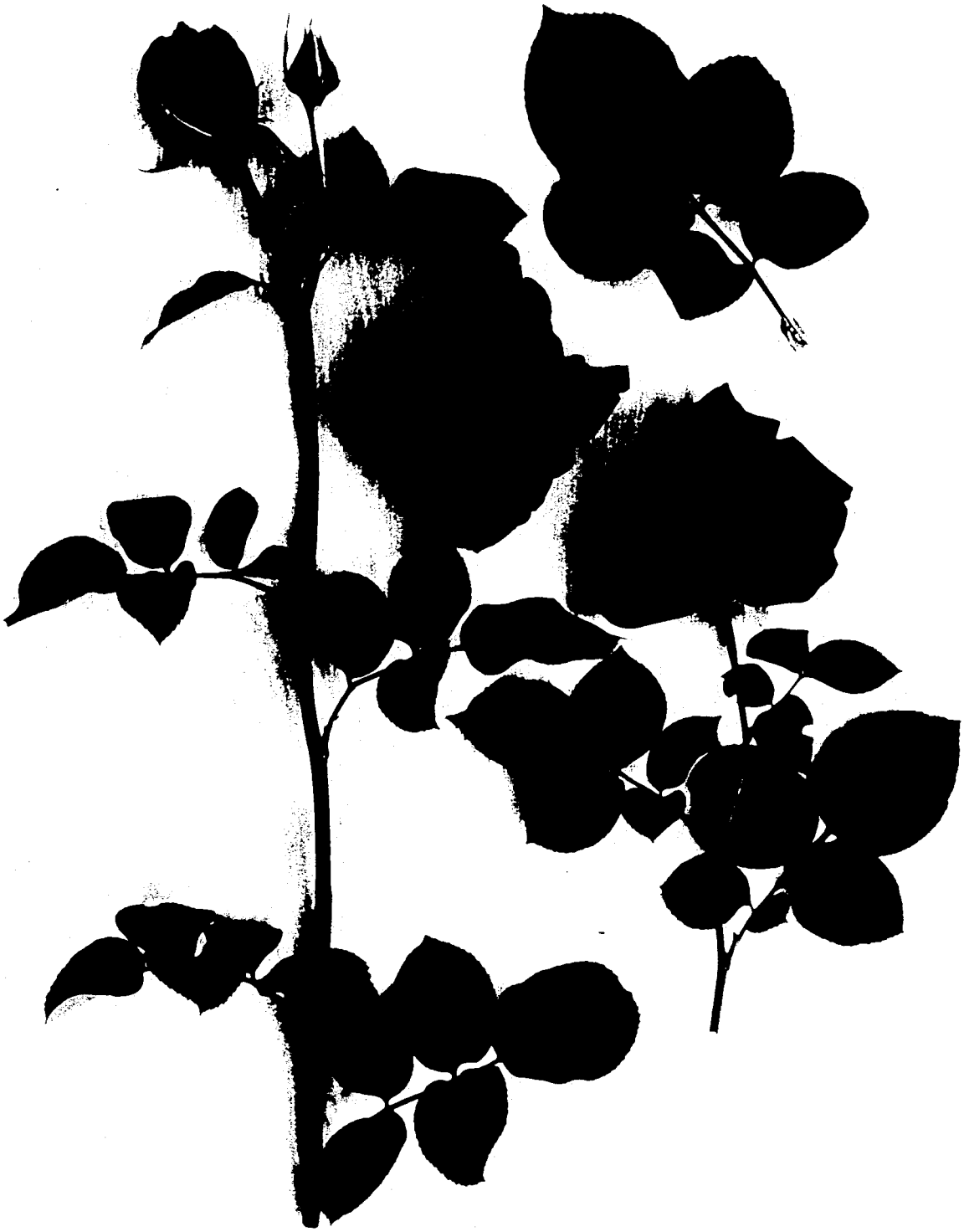

* * * * *